United States Patent [19]
Szabo et al.

[11] Patent Number: 5,534,006
[45] Date of Patent: Jul. 9, 1996

[54] KNOCKOUT TOOL FOR JOINT PROSTHESES

[75] Inventors: Zsolt Szabo, Feldmochinger Strasse, D-80993 München; Georg Seeberger, Pähl, both of Germany

[73] Assignee: Zsolt Szabo, Munich, Germany

[21] Appl. No.: 313,462

[22] Filed: Sep. 27, 1994

[30]  Foreign Application Priority Data

Sep. 27, 1993 [DE] Germany ............... 43 32 872.5

[51] Int. Cl.⁶ .................................................. A61B 17/92
[52] U.S. Cl. ............................................................ 606/100
[58] Field of Search ............................. 606/99, 100, 104

[56]     References Cited

U.S. PATENT DOCUMENTS

| 4,222,382 | 9/1980 | Antonsson et al. |
|---|---|---|
| 4,993,410 | 2/1991 | Kimsey ................................ 606/100 |

FOREIGN PATENT DOCUMENTS

| 0520940 | 12/1992 | European Pat. Off. |
|---|---|---|
| 2615097 | 11/1988 | France ............................ 606/99 |
| 2627983 | 9/1989 | France. |
| 2686016 | 7/1993 | France. |
| 3935518 | 5/1991 | Germany. |
| 4220970 | 7/1993 | Germany. |

*Primary Examiner*—Tamara L. Graysay
*Attorney, Agent, or Firm*—Browdy and Neimark

[57]     ABSTRACT

A knockout tool for joint prostheses has a curved tool head, which has a passage for receiving a prosthesis shaft and has a locking device which releasably blocks the prosthesis shaft in the passage, characterized in that the locking device has a blocking element engaging the passage, whose engagement position is adjustable for the sake of adaptation to various prosthesis shaft diameters, wherein an adjusting force, serving to adjust the engagement position and acting upon the blocking member, is transmitted along the curved tool head.

13 Claims, 5 Drawing Sheets ated 5,534,006

KNOCKOUT TOOL FOR JOINT PROSTHESES

FIELD OF THE INVENTION

The present invention relates to a tool for knocking out joint prostheses.

BACKGROUND OF THE INVENTION

A prosthesis knockout tool is shown in German Patent Application DE 42 20 970 A1. The tool head is curved in order to compensate for an angling of the prosthesis shaft relative to a center axis of the prosthesis, so that the joint prosthesis that has been inserted into the bone can be knocked out in the extension of the center axis of the prosthesis. The angle of curvature of the tool head is therefore essentially equivalent to the angling of the prosthesis shaft relative to the center axis of the prosthesis. Misalignment between the knockout force vector and the center axis of the prosthesis causes splintering of the bone surrounding the joint prosthesis, which is undesired.

The knockout tool known from German Patent Application DE 42 20 970 A1 has a tongue that is formed on a lever arm supported outside the tool head and is intended for engagement with a recess formed in the prosthesis shaft, in order to lock the prosthesis to the tool head. Hence that tool requires a large amount of space.

The prosthesis shafts of conventional joint prostheses are not standardized and have different diameters. However, previously known knockout tools do not adequately take such different prosthesis shaft diameters into account, and adaptation to various diameters is complicated. When such knockout tools are used with such prosthesis shafts of small diameter, the prosthesis shaft is not always locked in the tool head without play and form-fittingly.

It must also be taken into account that the pivot lever, supported outside the tool head in the previously known knockout tool, increases the space required by the tool considerably. Yet there is only limited space available for the knockout tool at the site of the operation.

SUMMARY OF THE INVENTION

Accordingly, the present invention has an object, among others, to overcome deficiencies in the prior art such as noted above.

An object of the present invention is therefore to further develop a knockout tool in such a way that different prosthesis diameters can easily be adjusted to in the tool head. A further object is that the knockout tool according to the invention occupy the least possible space, which should ideally be limited to the tool head.

According to the invention, the release position and the engagement position of the blocking member of the locking device that engages the passage are adjustable, such that prosthesis shafts of different diameters can be introduced into the passage and made to contact the blocking member. The cross-sectional area defined in the release position between the blocking member and the parts of the tool head that define the passage can thus be made larger and smaller. The release position of the blocking member is defined by the zero-play contact of the blocking member with the prosthesis shaft; from this release position, the blocking member is tightened into and firmly locked in the blocking position by some suitable means. The adjusting force brought to bear for actuating the blocking member to adjust the release position is transmitted by actuators in the tool head, thus making an adjusting device mounted outside the tool head unnecessary, and the transmission of force takes place in the tool head itself. This minimizes the space required for the tool head.

It is preferred that the tool head be smoothly curved. Smooth curvature of the tool head promotes the operative connection of the actuators, since the adjusting force can be transmitted essentially axially. With a smooth curvature, the normal forces operative in force transmission are minimized.

The tool head preferably has a longitudinal recess that opens into or overlaps with the passage, in which recess the actuators and the blocking member are disposed and guided. As a result, the tool head can be mounted and detached conveniently. The individual parts that form the tool head can easily be sterilized after being removed, which has enormous significance for medical applications.

Preferably the actuators and the blocking member are guided in opposed grooves formed in the tool head. These grooves are engaged with corresponding guide protrusions of the blocking member and the actuators, so that the blocking member and the actuators can be thrust axially into and removed axially from the longitudinal recess of the forklike tool head.

Preferably, an actuator is connected to a lever that serves to feed the blocking element forward into the locking position and to releasably block the blocking element in the locking position. The blocking member in a dual function is used both to transmit the adjusting force and to transmit the locking force. From the release position, defined as being in contact with the prosthesis shaft, the blocking member is pressed against the prosthesis shaft by axial tightening and locked in this locking position in such a way that the blocking member is arrested and cannot retreat. By embodying the actuator in a lever, an additional locking device for the blocking member is eliminated, and a space-saving minimal arrangement is created.

Preferably, the pivot shaft of the lever is formed in the actuator, so as to avoid one additional pivot shaft.

The actuator preferably has an eccentric engagement face, which defines an axial displacement position of the blocking element that is dependent on the pivot angle. The engagement face defines the contact of the actuator, embodied with a lever, with the following actuator or with the blocking member, so that the differing spacing of various angularly offset points on the engagement face from the pivot shaft results in a different displacement of the engagement face when the lever is swiveled.

Preferably, the actuator has two guide protrusions, which are longitudinally guided for displacement in internal grooves formed in the tool head; the guide protrusions embody a pivot shaft of the lever. The guide protrusions have the function on the one hand of guiding the actuator in order to transmit the adjusting force into the grooves of the tool head. On the other, they serve as a pivot shaft for the lever connected to the actuator, thereby once again creating a space-saving arrangement.

In a further embodiment, the actuators are embodied by balls or rollers, which are operatively connected to one another. The balls follow the curvature of the tool head in an especially space-saving and force-saving manner, since they have a slight diameter in comparison with the length of the tool head.

Preferably, an actuation rod, on which a hammer element is displaceably guided, is connected to the tool head. The hammer element strikes against a stop secured to the actuation rod, so that the impact brought to bear on this stop is transmitted directly, via the tool head and the prosthesis shaft, to the main body of the prosthesis, thereby releasing the latter from the bone.

Preferably, an adjusting rod is displaceably guided in the actuation rod and connected to the tool head in such a way that the adjusting force is brought to bear upon an outer actuator of the tool head. The adjusting rod is displaceably guided in the hollow actuation rod, preferably by a thread, so that by turning the knob connected to the adjusting rod, the adjusting rod is guided axially toward the outer actuator and feeds the actuator in the axial direction. After transmission by the further actuators, the adjusting force brought to bear by the adjusting rod thus reaches the blocking member.

In a further embodiment, which refers to the aforementioned embodiment with balls or rolls, the adjusting rod simultaneously serves to adjust the engagement position of the blocking element, for the sake of adaptation to different prosthesis shaft diameters, and to lock it. Here a lever connected to an actuator is omitted, and the adjusting force brought to bear on the actuators to actuate the blocking member acts, with suitable dimensioning, to tighten the blocking member into the locking position and to lock the blocking member in this position as well. For that purpose, the adjusting rod, which is guided in the actuation rod, can for instance be tightened and loosened by an eccentric lever or the like.

In a further preferred embodiment, a lever member is disposed on one end of the adjusting rod and is operatively connected to the adjusting rod in such a manner that swiveling of the lever member feeds the adjusting rod forward toward the tool head. In this way, the adjusting force generated by the lever member is transmitted along the adjusting rod and along the actuators onto the blocking member. The disposition of a lever member on an end of the adjusting rod opposite the tool head creates the possibility of an especially space-saving and ergonomically effective actuation of the knockout tool. Pivoting the lever member makes it possible to prestress the adjusting rod in the direction of the tool head, or to release it.

Preferably, the lever member is removable, so that alternative prestressing devices can also be mounted.

Further advantages, characteristics and possible applications of the present invention will become apparent from the ensuing description of a preferred exemplary embodiment in conjunction with the drawing.

DETAILED DESCRIPTION OF THE PREFERRED EMBODIMENTS

Figure 1:
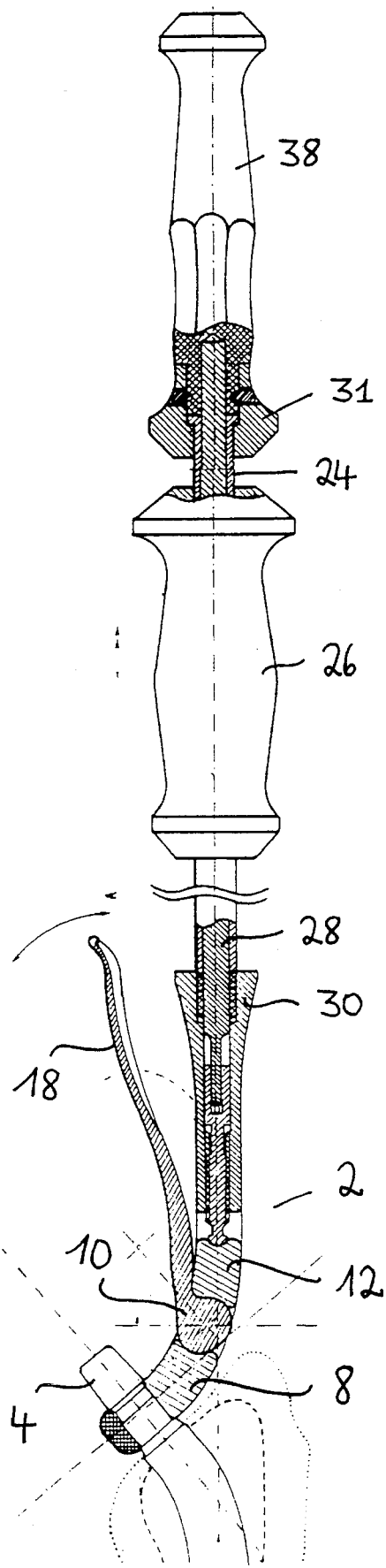
FIG. 1 is a cross sectional view through the knockout tool according to the present invention, mounted on the prothesis shaft.
Figure 2:
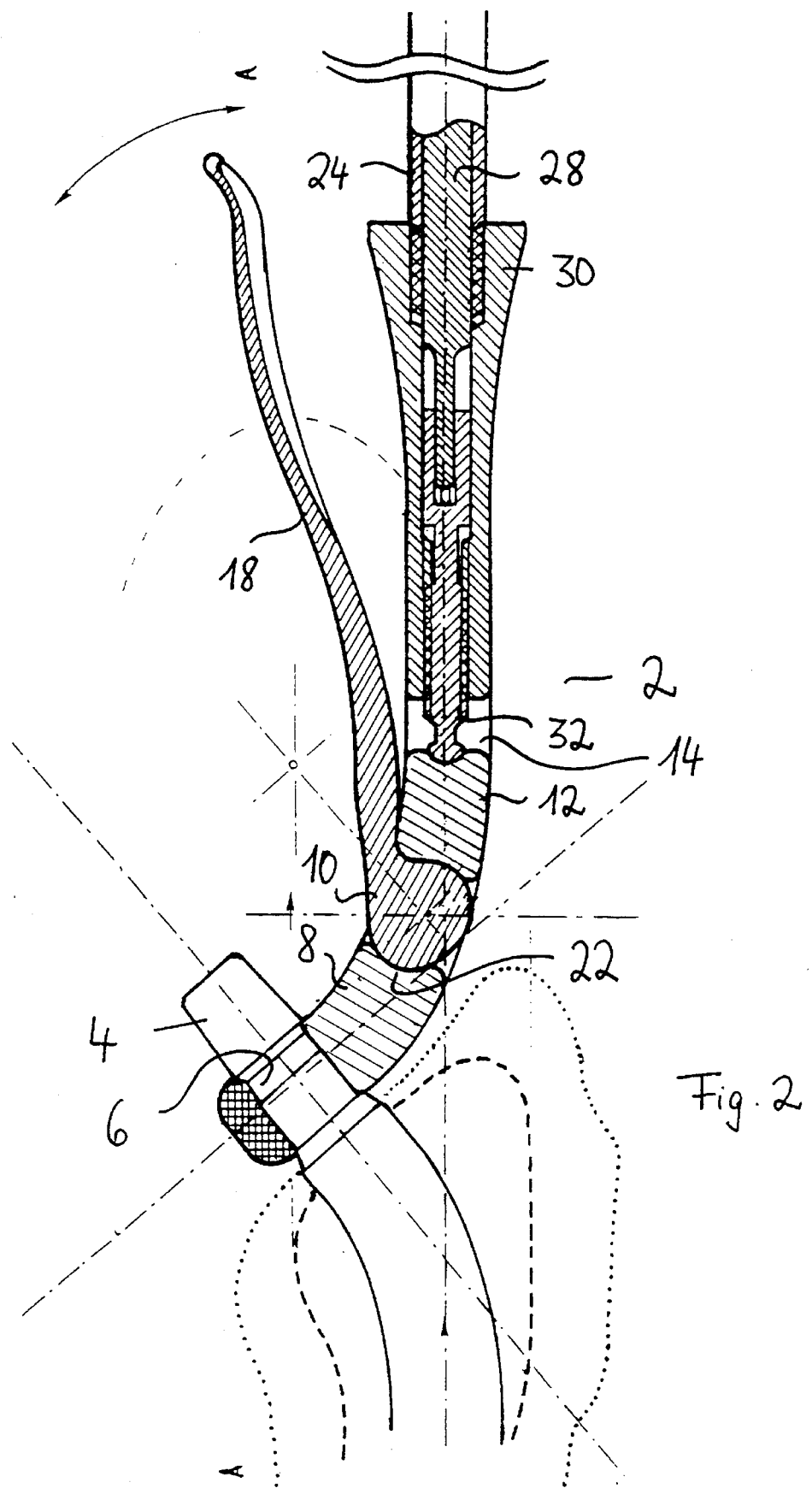
FIG. 2 is a detail showing the mounted tool head in cross section.
Figure 3:
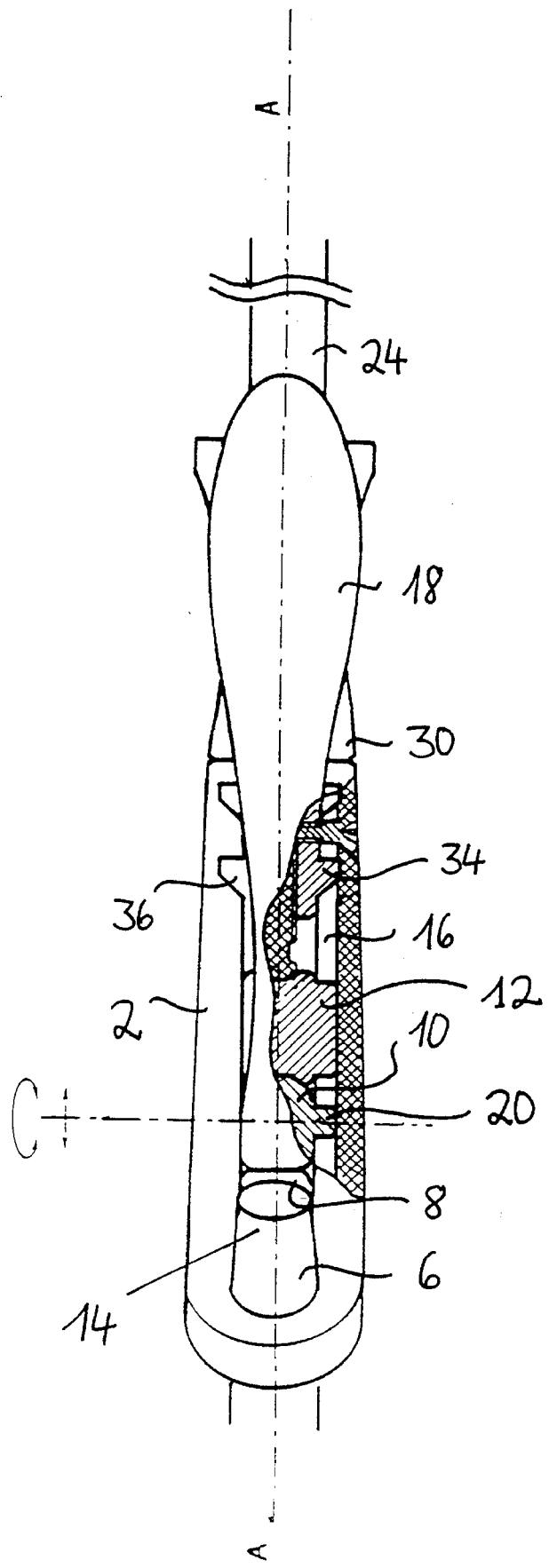
FIG. 3 is a plan view showing the tool head of FIG. 2 partly cut away.

The present invention relates to a knockout tool, shown in the drawing. The knockout tool is intended to be secured to a shaft 4 of a joint prosthesis that is inserted or fitted into a bone and is to be removed from the bone by the knockout tool.

The knockout tool comprises a tool head, which can be secured to the neck 4 of the prosthesis, and an actuation rod 24 connected to the tool head and on which a hammer element 26 is displaceably guided. Also permanently connected to the rod 24 is a stop 31 against which the hammer element 26 is guided in order to produce an axially oriented impact.

The tool head 2 is horseshoe- or fork-like in shape, with a longitudinal recess 14, which is intended to receive various actuators 8, 10, 12, and with a passage 6, widened opposite the longitudinal recess 14, that is intended to receive the shaft 4 of the prosthesis. The passage 6 has a circular cross section, except for the area of intersection with the longitudinal recess 14. In the side walls of the tool head 2 toward the longitudinal recess 14, two opposed, elongated, elliptically curved grooves 16 are formed, which serve to guide the actuators 8, 10, 12. The tool head 2, as FIG. 1 shows, is elliptically steadily curved or bent so as to compensate for a curvature between the shaft 4 of the prosthesis and the adjoining main body thereof, so that the impact force transmitted by the actuation rod 24 will be transmitted in the axial direction of the main body of the prosthesis. The grooves 16 are adapted to the curvature of the tool head 2 and likewise have a curved course.

A blocking element 8 is first introduced into the recess 14; it has opposed longitudinal ribs intended to be received in the corresponding internal grooves 16 in the tool head 2. As a result, the blocking element 8 can be introduced axially into the tool head 2. Since the grooves extend as far as the end of the passage 6 in the tool head 2, the path of the blocking element 8 inserted into the tool head 2 ends at the end of the longitudinal recess 14, or in the region of the (imaginary) line extending the cross section of the passage 6. However, the blocking element 8 can be fed even farther into the passage 6, for the sake of effective locking of prosthesis shafts of smaller diameter as well. For adaptation to the circular cross section of the prosthesis shaft 4, the blocking element 8 has an engagement face of circular-arc cross section for contact with the prosthesis shaft 4.

Behind the blocking member 8, a cam actuator 10 provided with a lever 18 is likewise introduced axially; it has two opposed guide protrusions 20, with which it is guided in the grooves 16 of the tool head 2. The lever 18 serves to tighten the blocking element 8 from a relief position, in which the neck 4 of the prosthesis can be introduced into the passage 6, into a locking position, in which the blocking member 8 is tightened against the neck 4 of the prosthesis and locked in that position. To that end, the actuator 10, connected to the lever 18, has an eccentric engagement face 22, which when the lever 18 is swiveled causes an increasing axial displacement of the blocking member 8 with an ensuing detent locking of the blocking element 8 in an essentially plane segment of the engagement face 22.

Behind the actuator 10, an outer actuator 12 is placed with its two opposed guide protrusions on the internal grooves 16 of the tool head 2. The actuator 12 is the last of the movable actuators. Action upon the outer actuator 12, through the mediation of the middle actuator 10, preadjusts the blocking element 8 in its position. The release position of the blocking element 8 can thus be varied by means of axial pressure on the outer actuator 12. A connecting and termination piece 30 is slipped onto the tool head at the termination of the tool head 2, behind the outer actuator 12. The connecting piece 30 has laterally protruding teeth, which are intended to be received in suitably shaped recesses 36 formed in the tool head 2. The connecting piece 30 is thus introduced into the tool head 2 from above and closes off the longitudinal recess 14, formed in the tool head 2, on its end opposite the passage 6. For actuation of the outer actuator 12, an elongated bore 32 is formed in the connecting piece 30, this bore being intended for engagement of an adjusting rod 28.

The connecting piece 30 is connected axially on its end to the actuation rod 24, as shown in FIG. 1. The adjusting rod 28 is guided axially within a hollow conduit in the actuation rod 24 and extends through the bore 32 of the connecting piece 30 so as to enter into contact with the outer actuator 12. The adjusting rod 28 is provided with a knob 38 on its other end, which when rotated rotates the adjusting rod 28 out of the threaded bore 32 formed in the connecting piece 30 and thus changes the axial position of engagement of the blocking member 8.

After the shaft 4 of the prosthesis has been introduced into the passage 6 of the tool head 2, the adjusting rod is first fed, by turning the knob 38, far enough that the blocking member 8 enters into contact with the neck 4 of the prosthesis in the passage 6. The lever 18 is then in its release position pointing away from the tool head 2. Once the blocking member 8 contacts the shaft 4 of the prosthesis, the lever 18 is swiveled back out of its release position into its locking position shown in FIG. 1, which is adjacent to the connecting piece 30 or oriented parallel with the tool head 2. In the process, the eccentric engagement face 22 of the actuator 10 is displaced against the blocking element 8 and biases the blocking element from its release position into its locking position, where the blocking element locks in detent fashion on an essentially plane segment of the engagement face 22 of the actuator 10. The tool head 2 is now firmly locked to the prosthesis, and the prosthesis can now be removed from the bone by hammer strikes of the hammer element 26 against the stop 31. For loosening the tool head 2 and the shaft 4 of the prosthesis, the lever 18 is swiveled out of its locking position into its release position in which it protrudes from the tool head 2 and in which the blocking element is in movable contact with the shaft 4 of the prosthesis. As a result of the retreating engagement face 22 of the lever 18 and the turning of the knob 38, the blocking element 8 is given some play, so that the shaft 4 of the prosthesis can conveniently be pulled out of the passage 6.

Figure 4:
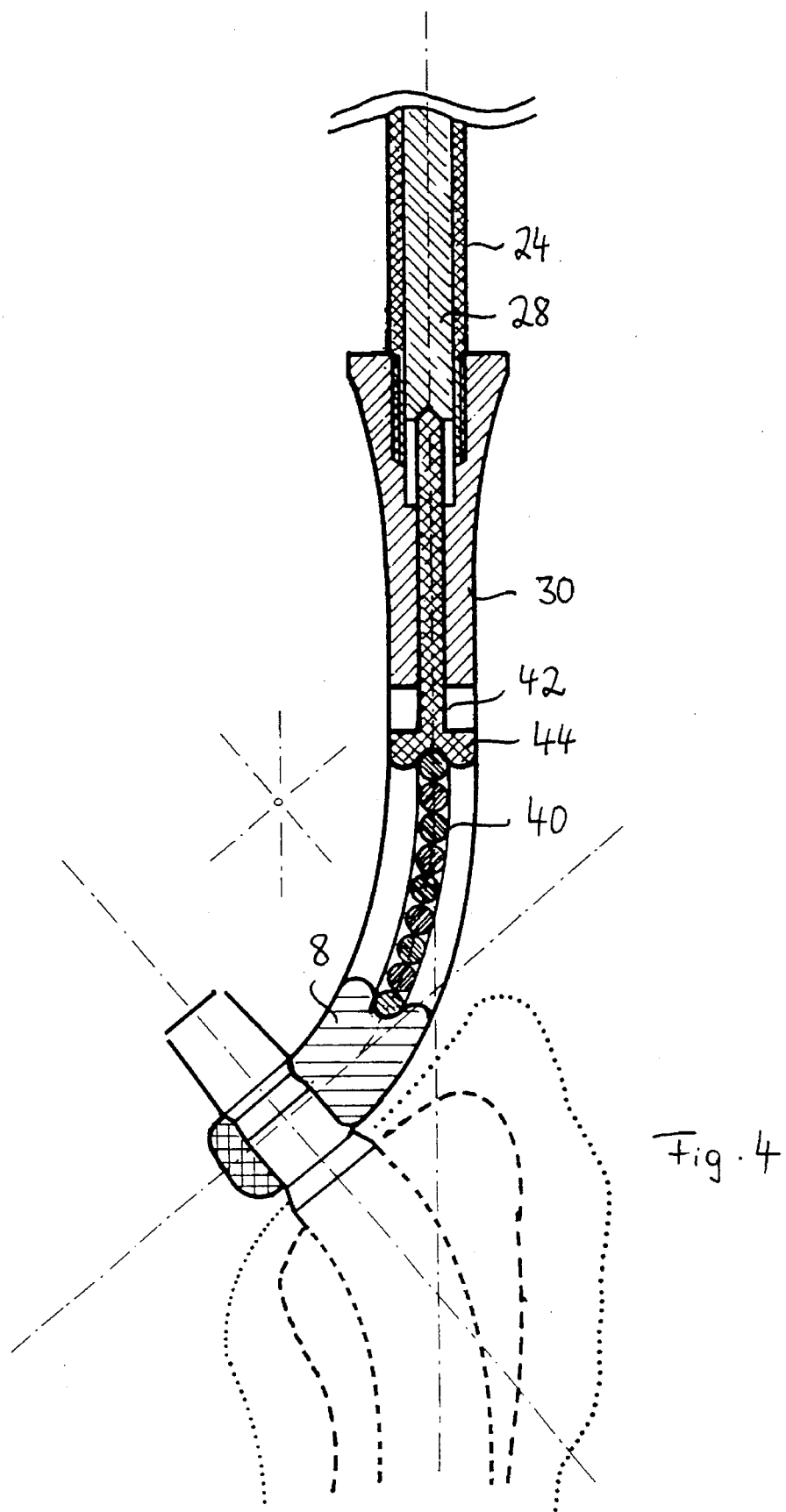
FIG. 4 is a cross sectional view of a modified embodiment of the tool head with rollers.

The embodiment of the present invention of the knockout tool shown in FIG. 4 has a tool head equipped with rollers 40, the rollers 40 being supported and guided in the grooves 16 formed in the tool head. The rollers 40 thus serve as actuators disposed one after the other, which transmit to the blocking element 8 an adjusting force received axially from the adjusting rod 28. The rollers 40 follow the curvature of the tool and are disposed such that they are operatively connected to one another.

For connecting the adjusting rod 28 and the rollers 40, a thrust rod 42 guided in the connecting piece 30 is provided, which is connected on one end to the adjusting rod 28 and which on its other end has a head 44, embodied with an indentation, that serves to receive the rollers. The head 44 has an elongated indentation in which the rollers are disposed and against which the rollers are braced. The adjusting rod 28 thus by mediation of the thrust rod 42 transmits an axial adjusting and locking force to the rollers 40. Since in this embodiment there is no separate locking element in the form of a lever in the actuators, the locking force, like the adjusting force, is transmitted by the adjusting rod 28 to the rollers and thus to the blocking element 8. Thus the adjustment of the engagement position and the locking of the blocking element in the locking position are effected solely by way of an axial displacement of the adjusting rod 28. By way of example (in a manner not shown), the adjusting rod can be connected to an eccentric lever which by changing position axially feeds the adjusting rod 28 forward or pushes it backward. The eccentric lever may be prestressed into a release position by means of spring force.

Figure 5:
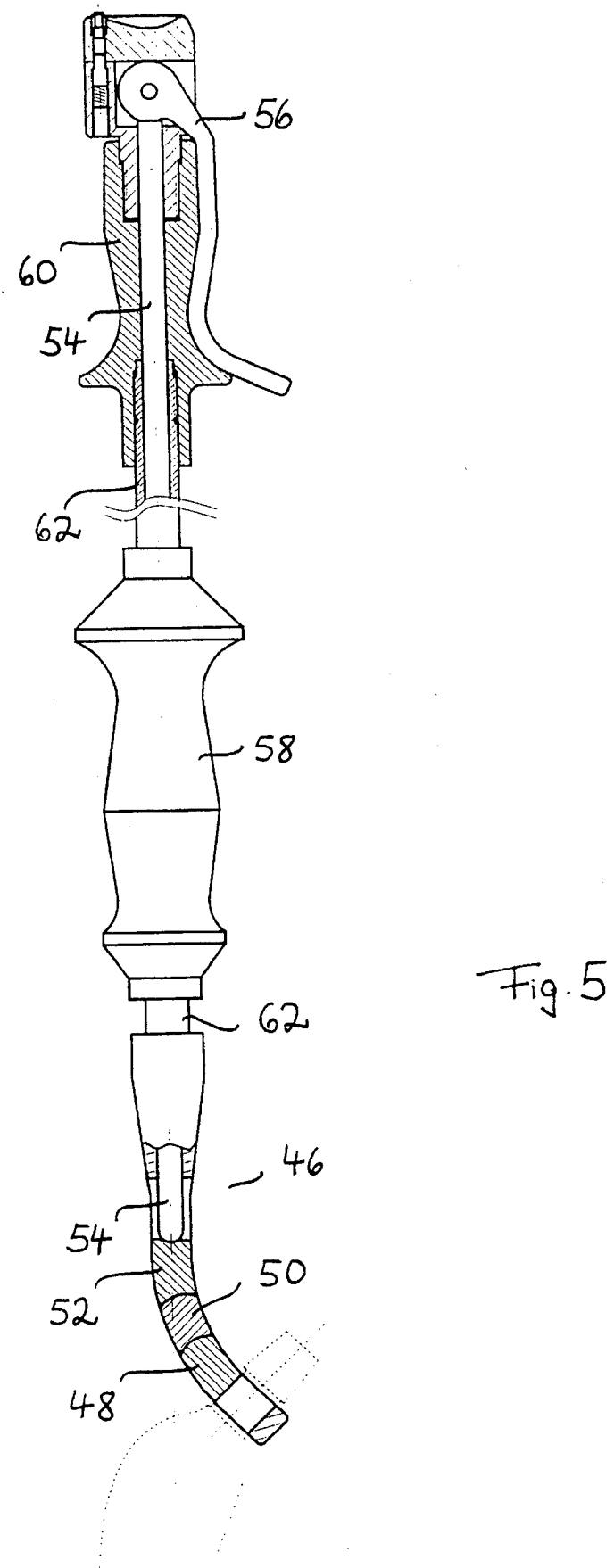
FIG. 5 is a partially cross sectional view of an alternative embodiment of the present invention.

FIG. 5 shows an alternative embodiment of the knockout tool of FIG. 1. A tool head 46 is connected to an actuation rod 62, on which a hammer element 58 slides. The hammer element 58 is displaceably guided on the actuation rod 62, and on one end of its travel path comes to rest against a shoulder of the tool head 46, so as to transmit an axial knockout pulse in this way longitudinally of the tool head. An adjusting rod 54 is movably guided in the internal cavity of the actuation rod 62; the adjusting rod extends on one end into the tool head 46 and comes to rest against an actuator 52 which is axially guided for displacement along the tool head. In addition to the actuator 52, and in contact with it, a further actuator 50 and, resting on the actuator 50, a blocking member 48 are disposed in the tool head 46; the blocking member engages a passage formed in the tool head in order to lock a prosthesis shaft that has been introduced. The adjusting force of the adjusting rod 54 leads to an axial displacement of the actuators or of the blocking element along the curved tool head 46, so that the blocking element can perform its locking function. On the end of the actuation rod 62 opposite the tool head 46, a handle 60, suitable for manipulation by hand, is connected to the actuation rod 62. The adjusting rod 54 extends through the handle 60 and out of it.

On the end of the handle opposite the actuation rod 62, a lever fitting is inserted into a suitable indentation of the handle; the lever fitting has a lever member 56. The lever member 56 is comparable to the lever 18 of FIG. 1 already described above, and so a more-detailed description of the lever member 56 may be dispensed with. As a result, by the provision of an eccentric engagement face on the lever member 56, this member is put into a position in which by swiveling it can exert an axially oriented adjusting force upon the adjusting rod 54, and as a result the blocking member 48 is fed in the tool head 46 and made to engage the recess. The level fitting is removable, so that it is also possible for the adjusting rod 54 to be fed forward or pulled back again in some other way.

The handle 60 can be screwed together with the guide tube or actuation rod 62 for the sake of variable adjustment of the adjusting rod 54.

The foregoing description of the specific embodiments will so fully reveal the general nature of the invention that others can, by applying current knowledge, readily modify and/or adapt for various applications such specific embodiments, without departing from the generic concepts, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A knockout tool for joint prostheses, the knockout tool adapted for gripping a prosthesis shaft (4), the knockout tool comprising:

a curved tool head (2), the tool head having a passage (6) therethrough for receiving the prosthesis shaft; and a locking device (8, 10, 12) to releasably block the prosthesis shaft within the passage, the locking device further comprising a blocking member (8) engaging the passage, the blocking member having a position adjustable in an axial direction transverse to a length of the prosthesis shaft by actuator means disposed within the tool head for adjusting a position of the blocking member, the actuator means including actuators axially displaceable within the tool head;

whereby a force transmitted axially along said actuators adjusts the position of the blocking member.

2. A knockout tool for joint prostheses, the knockout tool adapted for gripping a prosthesis shaft (4), the knockout tool comprising:

a curved tool head (2), the tool head having a passage (6) therethrough for receiving the prosthesis shaft; and a locking device (8, 10, 12) to releasably block the prosthesis shaft within the passage, the locking device further comprising a blocking member (8) engaging the passage, the blocking member having a position adjustable by actuator means disposed within the tool head for adjusting a position of the blocking member, the actuator means including actuators axially displaceable within the tool head, whereby a force transmitted axially along said actuators adjusts the position of the blocking member; and wherein the tool head is smoothly curved and the actuator means includes an axial longitudinal recess (14) opening into the passage; the actuators and the blocking member being disposed within the recess.

3. The knockout tool of claim 2, wherein the actuators and the blocking member are guided in opposed grooves (16) formed in the tool head.

4. A knockout tool for joint prostheses, the knockout tool adapted for gripping a prosthesis shaft (4), the knockout tool comprising:

a curved tool head (2), the tool head having a passage (6) therethrough for receiving the prosthesis shaft; and a locking device (8, 10, 12) to releasably block the prosthesis shaft within the passage, the locking device further comprising a blocking member (8) engaging the passage, the blocking member having a position adjustable by actuator means disposed within the tool head for adjusting a position of the blocking member, the actuator means including actuators axially displaceable within the tool head, whereby a force transmitted axially along said actuators adjusts the position of the blocking member; and wherein the actuators further comprise an inner actuator (10) and an outer actuator (12), the inner actuator including a pivot shaft (20), the inner actuator being connected to a lever (18) that acts to feed the blocking element into a locking position and to releasably block the blocking element in the locking position.

5. A knockout tool for joint prostheses, the knockout tool adapted for gripping a prosthesis shaft (4), the knockout tool comprising:

a curved tool head (2), the tool head having a passage (6) therethrough for receiving the prosthesis shaft; and a locking device (8, 10, 12) to releasably block the prosthesis shaft within the passage, the locking device further comprising a blocking member (8) engaging the passage, the blocking member having a position adjustable by actuator means disposed within the tool head for adjusting a position of the blocking member, the actuator means including actuators axially displaceable within the tool head, whereby a force transmitted axially along said actuators adjusts the position of the blocking member; and wherein the actuators include selectively balls and rollers (40).

6. A knockout tool for joint prostheses, the knockout tool adapted for gripping a prosthesis shaft (4), the knockout tool comprising:

a curved tool head (2), the tool head having a passage (6) therethrough for receiving the prosthesis shaft; and a locking device (8, 10, 12) to releasably block the prosthesis shaft within the passage, the locking device further comprising a blocking member (8) engaging the passage, the blocking member having a position adjustable by actuator means disposed within the tool head for adjusting a position of the blocking member, the actuator means including actuators axially displaceable within the tool head, whereby a force transmitted axially along said actuators adjusts the position of the blocking member;

further comprising an actuation rod (24, 62) connected to the tool head and a hammer element (26, 58) slidably mounted on the actuation rod; and wherein an adjusting rod (28, 54) is slidably mounted in the actuation rod and is connected to the tool head (2) such that the adjusting force is brought to bear upon an outer actuator (12) of the tool head.

7. The knockout tool of claim 6, wherein the adjusting rod simultaneously acts to adjust an engagement position of the blocking element for adaptation to different shaft diameters of the prosthesis shaft and to lock the blocking element.

8. The knockout tool of claim 6, wherein a lever member (56) is disposed on an end of the adjusting rod and is operatively connected to the adjusting rod such that swiveling of the lever member displaces the adjusting rod toward the tool head.

9. The knockout tool of claim 8, wherein the lever member is removable.

10. A knockout tool for gripping a joint prosthesis shaft extending from a bone and for removing a prosthesis of the joint prosthesis shaft from the bone, the knockout tool comprising:

a tool head further including an actuating end and a gripping end, an exterior surface having a smooth curve, a passage proximal the gripping end and extending from the exterior surface to a distal side of the tool head, and an interior channel communicating with the passage;

a blocking member slidably disposed within the channel proximal the passage, the blocking member adapted together with the passage for gripping the prosthesis shaft therebetween;

actuator elements slidably disposed within the channel, the actuator elements including an inner actuator element proximal the blocking member and an outer actuator element distal the blocking member;

blocking force means for releasably locking the blocking member against the prosthesis shaft; and dislodging means for applying knockout force to the prosthesis shaft for removing the prosthesis.

11. The knockout tool according to claim 10, wherein the dislodging means includes a hammer slidably mounted on a rod, the rod connected to the actuating end of the tool head.

12. The knockout tool according to claim 11, wherein the passage and the blocking member are jointly formed such that the prosthesis shaft is perpendicular to the exterior surface when the blocking member is locked against the prosthesis shaft.

13. The knockout tool according to claim 11, wherein the rod is parallel to a tangent to the exterior surface at the actuating end.

* * * * *